(12) United States Patent
Harper et al.

(10) Patent No.: US 12,325,856 B2
(45) Date of Patent: Jun. 10, 2025

(54) RECOMBINANT VIRUS PRODUCTS AND METHODS FOR INHIBITION OF EXPRESSION OF MYOTILIN

(71) Applicant: NATIONWIDE CHILDREN'S HOSPITAL, INC., Columbus, OH (US)

(72) Inventors: Scott Quenton Harper, Powell, OH (US); Jian Liu, Savoy, IL (US)

(73) Assignee: RESEARCH INSTITUTE AT NATIONWIDE CHILDREN'S HOSPITAL, Columbus, OH (US)

( * ) Notice: Subject to any disclaimer, the term of this patent is extended or adjusted under 35 U.S.C. 154(b) by 664 days.

(21) Appl. No.: 17/374,147

(22) Filed: Jul. 13, 2021

(65) Prior Publication Data

US 2022/0064641 A1 Mar. 3, 2022

Related U.S. Application Data

(60) Division of application No. 16/144,432, filed on Sep. 27, 2018, now Pat. No. 11,091,760, which is a continuation of application No. 14/853,517, filed on Sep. 14, 2015, now Pat. No. 10,196,636, which is a continuation-in-part of application No. 14/058,909, filed on Oct. 21, 2013, now Pat. No. 9,133,482, which is a continuation-in-part of application No. PCT/US2012/034408, filed on Apr. 20, 2012.

(60) Provisional application No. 61/478,012, filed on Apr. 21, 2011.

(51) Int. Cl.
| | | |
|---|---|---|
| *C12N 15/86* | (2006.01) | |
| *C07K 14/47* | (2006.01) | |
| *C12N 15/113* | (2010.01) | |

(52) U.S. Cl.
CPC ........ *C12N 15/113* (2013.01); *C07K 14/4707* (2013.01); *C12N 15/1138* (2013.01); *C12N 15/86* (2013.01); *C12N 2310/14* (2013.01); *C12N 2310/141* (2013.01); *C12N 2320/32* (2013.01); *C12N 2330/51* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 5,173,414 A | 12/1992 | Lebkowski et al. | |
| 5,658,776 A | 8/1997 | Flotte et al. | |
| 5,786,211 A | 7/1998 | Johnson | |
| 5,871,982 A | 2/1999 | Wilson et al. | |
| 6,258,595 B1 | 7/2001 | Gao et al. | |
| 6,458,929 B1 | 10/2002 | Carpen et al. | |
| 6,566,118 B1 | 5/2003 | Atkinson et al. | |
| 2005/0276787 A1 | 12/2005 | Couto et al. | |
| 2007/0244067 A1 | 10/2007 | Budker et al. | |
| 2008/0213182 A1 | 9/2008 | Swanson et al. | |
| 2014/0045925 A1 | 2/2014 | Harper et al. | |
| 2019/0249174 A1 | 8/2019 | Harper et al. | |

FOREIGN PATENT DOCUMENTS

| | | |
|---|---|---|
| KR | 10-2002-0028904 | 4/2002 |
| WO | WO-1995/13365 A1 | 5/1995 |
| WO | WO-1995/13392 A1 | 5/1995 |
| WO | WO-1996/17947 A1 | 6/1996 |
| WO | WO-1997/06243 A1 | 2/1997 |
| WO | WO-1997/08298 A1 | 3/1997 |
| WO | WO-1997/09441 A2 | 3/1997 |
| WO | WO-1997/21825 A1 | 6/1997 |
| WO | WO-1998/09657 A2 | 3/1998 |
| WO | WO-1999/011764 A2 | 3/1999 |
| WO | WO-2002/053703 A2 | 7/2002 |
| WO | WO-2009/097129 A1 | 8/2009 |
| WO | WO-2009/137006 A2 | 11/2009 |

OTHER PUBLICATIONS

Carter, Adeno-associated virus vectors. *Curr. Opin. Biotechnol.*, 3: 533-9 (1992).
Clark et al., A stable cell line carrying adenovirus-inducible rep and cap genes allows for infectivity titration of adeno-associated virus vectors, *Gene Therapy*, 3:1124-32 (1996).
Clark et al., Highly purified recombinant adeno-associated virus vectors are biologically active and free of detectable helper and wild-type viruses, *Hum. Gene Ther.*, 10(6):1031-9 (1999).
Cserjesi et al., Myogenin induces the myocyte-specific enhancer binding factor MEF-2 independently of other muscle-specific gene products, *Mol. Cell Biol.*, 11:4854-62 (1991).
De et al., High levels of persistent expression of alpha1-antitrypsin mediated by the nonhuman primate serotype rh. 10 adeno-associated virus despite preexisting immunity to common human adeno-associated viruses, *Mol. Ther.*, 13(1):67-76 (2006).
Duan (Ed.), Section 7.3 of Chapter 7 in Muscle Gene Therapy, Springer Science Business Media, LLC (2010).
Fechner et al., Cardiac-targeted RNA interference mediated by an AAV9 vector improves cardiac function in coxsackievirus B3 cardiomyopathy, *J. Mol. Med.*, 86:987-97 (2008).
Gao et al., Clades of Adeno-associated viruses are widely disseminated in human tissues, *J. Virol.*, 78:6381-8 (2004).
Garvey et al., Patho-Genetic Characterization of the Muscular Dystrophy Gene Myotilin, *Duke University*, 137-8 (2007).
Garvey et al., Transgenic mice expressing the myotilin T57I mutation unite the pathology associated with LGMD1A and MFM, *Hum. Mol. Genet.*, 15:2348-62 (2006).

(Continued)

*Primary Examiner* — Michael D Burkhart
(74) *Attorney, Agent, or Firm* — MARSHALL, GERSTEIN & BORUN LLP

(57) ABSTRACT

The present invention relates to RNA interference-based methods for inhibiting the expression of the myotilin gene. Recombinant adeno-associated viruses of the invention deliver DNAs encoding microRNAs that knock down the expression of myotilin. The methods have application in the treatment of muscular dystrophies such as Limb Girdle Muscular Dystrophy Type 1A.

10 Claims, 7 Drawing Sheets
(5 of 7 Drawing Sheet(s) Filed in Color)
Specification includes a Sequence Listing.

(56) References Cited

OTHER PUBLICATIONS

GenBank Accession No. AF085716, Adeno-associated virus 5 DNA binding trs helicase (Rep22) and capsid protein (VP1) genes, dated Feb. 10, 1999.
Genbank Accession No. AX753246, Sequence 1 from Patent EP1310571, dated Jun. 23, 2003.
Genbank Accession No. AX753249, Sequence 4 from Patent EP1310571, dated Jun. 23, 2003.
GenBank Accession No. NC_001401, Adeno-associated virus—2, complete genome, dated Aug. 1, 2000.
GenBank Accession No. NC_001829, Adeno-associated virus—4, complete genome, dated Aug. 1, 2000.
GenBank Accession No. NC_001862, Adeno-associated virus 6, complete genome, dated, Jan. 12, 2004.
GenBank Accession No. NC_002077, Adeno-associated virus—1, complete genome, dated Aug. 1, 2000.
Hauser et al., Myotilin is mutated in limb girdle muscular dystrophy 1A, *Hum. Mol. Genet.*, 9:2141-7 (2000).
Hauser et al., myotilin Mutation found in second pedigree with LGMD1A, *Am. J. Hum. Genet*, 71:1428-32 (2002).
Hermonat et al., Use of adeno-associated virus as a mammalian DNA cloning vector: transduction of neomycin resistance into mammalian tissue culture cells, *Proc. Natl. Acad. Sci. USA*, 81:6466 (1984).
International Preliminary Report on Patentability, PCT/US2012/034408 (Oct. 22, 2013).
International Search Report and Written Opinion, PCT/US2012/034408 (Nov. 1, 2012).
Johnson et al., Muscle creatine kinase sequence elements regulating skeletal and cardiac muscle expression in transgenic mice, *Mol. Cell Biol.*, 9:3393-9 (1989).
Laughlin et al., Cloning of infectious adeno-associated virus genomes in bacterial plasmids, *Gene*, 23:65-73 (1983).
Lebkowski et al., Adeno-associated virus: a vector system for efficient introduction and integration of DNA into a variety of mammalian cell types, *Mol. Cell. Biol.*, 8(10):3988-96 (1988).
Liu et al., Abstract T.O.1: RNAi therapy for LGMD1A, *Neuromusc. Disorders*, 22:9-10 (2012).
Liu et al., RNAi-mediated Gene Silencing of Mutant Myotilin Impromes Myopathy in LGMD1A Mice, *Molec. Ther. Nuc. Acids*, 3(4):1-10 (2014).
Liu et al., RNAi-based Gene Therapy for Dominant Limb Girdle Muscular Dystrophies, *Curr. Gene. Ther.*, 12(4):304-14 (2012).
Mader et al., A steroid-inducible promoter for the controlled overexpression of cloned genes in eukaryotic cells, *Proc. Natl. Acad. Sci. USA*, 90:5603-7 (1993).
McCarty, Self-complementary AAV vectors; advances and applications, *Mol. Ther.*, 16(10):1648-56 (2008).
McLaughlin et al., Adeno-associated virus general transduction vectors: analysis of proviral structures, *J. Virol.*, 62:1963 (1988).

Mori et al., Two novel adeno-associated viruses from cynomolgus monkey: pseudotyping characterization of capsid protein, *Virology*, 330(2):375-83 (2004).
Muscat et al., Multiple 5'-Flanking regions of the human alpha-skeletal actin gene synergistically modulate muscle-specific expression, *Mol. Cell. Biol.*, 7:4089-99 (1987).
Muzyczka, Use of adeno-associated virus as a general transduction vector for mammalian cells, *Curr. Top. Microbiol. Immunol.*, 158:97-129 (1992).
Paul et al., Increased viral titer through concentration of viral harvests from retroviral packaging lines, *Human Gene Therapy*, 4:609-15 (1993).
Perrin et al., An experimental rabies vaccine produced with a new BHK-21 suspension cell culture process: use of serum-free medium and perfusion-reactor system, *Vaccine*, 13:1244-50 (1995).
Samulski et al. Cloning of adeno-associated virus into pBR322: rescue of intact virus from the recombinant plasmid in human cells, *Proc. Natl. Acad. Sci. USA*, 79:2077-81 (1982).
Samulski et al., Helper-free stocks of recombinant adeno-associated viruses: normal integration does not require viral gene expression, *J. Virol.*, 63:3822-8 (1989).
Schnepp et al., Highly purified recombinant adeno-associated virus vectors. Preparation and quantitation, *Methods Mol. Med.*, 69:427-43 (2002).
Semenza et al., Hypoxia-inducible nuclear factors bind to an enhancer element located 3' to the human erythropoietin gene, *Proc. Natl. Acad. Sci. USA*, 88:5680-4 (1991).
Senapathy et al., Molecular cloning of adeno-associated virus variant genomes and generation of infectious virus by recombination in mammalian cells, *J. Biol. Chem.*, 259:4661-6 (1984).
Shalaby et al., Defective myotilin homodimerization caused by a novel mutation in MYOT exon 9 in the first Japanese limb girdle muscular dystrophy 1A patient, *J. Neuropathol. Exp. Neurol.*, 68:701-7 (2009).
Snyder et al., Efficient and Stable adeno-Associated Virus-Mediated Transduction in the Skeletal Muscle of Adult Immunocompetent Mice, *Hum. Gene Ther.*, 8(16):1891-900 (1997).
Srivastava et al., Nucleotide sequence and organization of the adeno-associated virus 2 genome, *J. Virol.*, 45:555-64 (1983).
Supplemental European Search Report, EP 12774899.4, Dated Dec. 10, 2014.
Tang et al., AAV-Directed Muscular dystrophy Gene Therapy, *Exp. Opin. Biol. Ther.*, 10(3):395-408 (2010).
Tratschin et al., A human parvovirus, adeno-associated virus, as a eucaryotic vector: transient expression and encapsidation of the procaryotic gene for chloramphenicol acetyltransferase, *Mol. Cell. Biol.*, 4:2072 (1984).
Tratschin et al., Adeno-associated virus vector for high-frequency integration, expression, and rescue of genes in mammalian cells, *Mol. Cell. Biol.*, 5:3251 (1985).
Wallace et al., Chapter 7: RNAi Therapy for Dominant Muscular Dystrophis and Other Myopathies, *Mus. Gene Ther.*, 99-115 (2010).
Wang et al., Construction and analysis of compact muscle-specific promoters for AAV vectors, *Gene Therapy*, 15:1489-99 (2008).
Weintraub et al., The myoD gene family: nodal point during specification of the muscle cell lineage, *Science*, 251:761-6 (1991).

Figure 1

Human C450T myotilin sequence (target sites are underlined and highlighted)

GGGAAGGAGATGCCTCTTCCTTCCCTTCAATAGTGGGTTAAACCCAGCTGGCA
CCCTCTGGAACTACGGGAACAATATTCTTCAAGAGAAGGTCACTCTACCAAAG
CCAGGAGCACAGTATTCTCAGGATCTCAACAAGGAAGAGCAGACCAAGGTTGC
TTCTGATTCCTTACAACCTTCCGTAATTCCAGGCTTGTGGCCCCAAATTCAGG
GCCCCACCCTTCCAGGAACAAATCATTATAGTAATAATTTGCCTTCATCTTCC
ATATACCAACTAAGCATGTTTAACTACGAACGTCCAAAACACTTCATCCAGTC
CCAAAACCCATGTGGCTCCAGATTGCAGCCTCCTGGACCAGAAACCTCCAGCT
TCTCTAGCCAGACCAAACAGTCTTCCATTATCATCCAGCCCCGCCAGTGTACA
GAGCAAAGATTTTCTGCCTCCTCAATACTGAGCTCTCACATCACCATGTCCTC
CTCTGCTTTCCCTGCTTCTCCCAAGCAGCATGCTGGCTCCAACCCAGGCCAAA
GGGTTACAACCACCTATAACCAGTCCCCAGCCAGCTTCCTCAGCTCCATATTA
CCATCACA592GCCTGATTACAATAGCAGTAAAATCCCTTCCGCTATGGATTC
CAACTATCAACAGTCCTCAGCTGGCCAACCTATAAATGCAAAGCCATCCCAAA
CTGCAAATGCTAAGCCCATACCAAGAACTCCTGATCATGAAATACAAGGATCA
AAAGAAGCTTTGATTCAAGATTTGGAAAGAAAGCTGAAATGCAAGGACACCCT
TCTTCATAATGGAAATCAACGTCTAACATATGAAGAGAAGATGGCTCGCAGAT
TGCTAGGACCACAGAATGCAGCTGCTGTGTTTCAAGCTCAGGATGACAGTGGT
GCACAAGACTCGCAGCAACACAACTCAGAACATGCGCGACTGCAAGTTCCTAC
ATCACAAGTAAGAAGTAGATCAACCTCAAGGGGAGATGTGAATGATCAGGATG
CAATCCAGGAGAAATTTTACCCACCACGTTTCATTCAAGTGCCAGAGAACATG
TCGATTGATGAAGGAAGATTCTGCAGAATGGACTTCAAAGTGAGTGGACTGCC
AGCTCCTGATGTGTCATGGTATCTAAATGGAAGAACAGTTCAATCAGATGATT
TGCACAAAATGATAGTGTCTGAGAAGGGTCTTCATTCACTCATCTTTGAAGTA
GTCAGAGCTTCAGATGCAGGGGCTTATGCATGTGTTGCCAAGAATAGAGCAGG
AGAAGCCACCTTCACTGTGCA1291GCTGGATGTCCTTGCAAAAGAACATAAA
AG1321AGCACCAATGTTTATCTACAAACCACAGAGCAAAAAGTTTTAGA13
66GGGAGATTCAGTGAAACTAGAATGCCAGATCTCGGCTATACCTCCACCAAA
GCTTTTCTGGAAAAGAAATAATGAAATGGTACAATTCAACACTGACCGAATAA
GCTTATATCAAGATAACACT1490GGAAGAGTTACTTTACTGATAAAAGATGT
AAACAAGAAAGATGCTGGGTGGTATACTGTGTCAGCAGTTAATGAAGCTGGAG
TGACTACATGTAACACAAGATTAGACGTTAC1603GGCACGTCCAAACCAAAC
TCTTCCAGCTCCTAAGCAGTTACGGGTTCGACCAACATTCAGCAAATATTTAG
CACTTAATGGGAAAGGTTTGAATGTAAAACAAGCTTTTAACCCAGAAGGAGAA
TTTCAGCGTTTGGCAGCTCAATCTGGACTCTATGAAAGTGAAGAACTTTAATA
ACTTTACCAACATTGGAAAACAGCCAACTACACCATTAGTAATATATTTGATT
ACATTTTTTTGAAATTAATCCATAGCTGTATTAACAGATTATGGTTTTAATTA
GGTAATATAGTTAATATATATTTATAATATTATTTATCCTTTGACTCTTGCAC
ATTCTATGTACCCCTCCGATTTGTGAAGCCTACAGGAAATCTGGGTATATGGA
TTTGTAACTGCAGAAGACTATCTTAAAATACAGGATTTTAACATTTAAGTCAT
GCACATTTAACAATTACAGGTTATAAATTAGTATCAACTTTTTAAACACATCT
AATGCTTGTAATAACGTTTACTGGTACTGCTTTCTAAATACTGTTTTACCCGT
TTTCTCTTGTAGGAATACTAACATGGTATAGATTATCTGAGTGTTCCACAGTT
GTATGTCAAAAGAAAATAAAATTCAAATATTTAAAACGGA

Figure 2
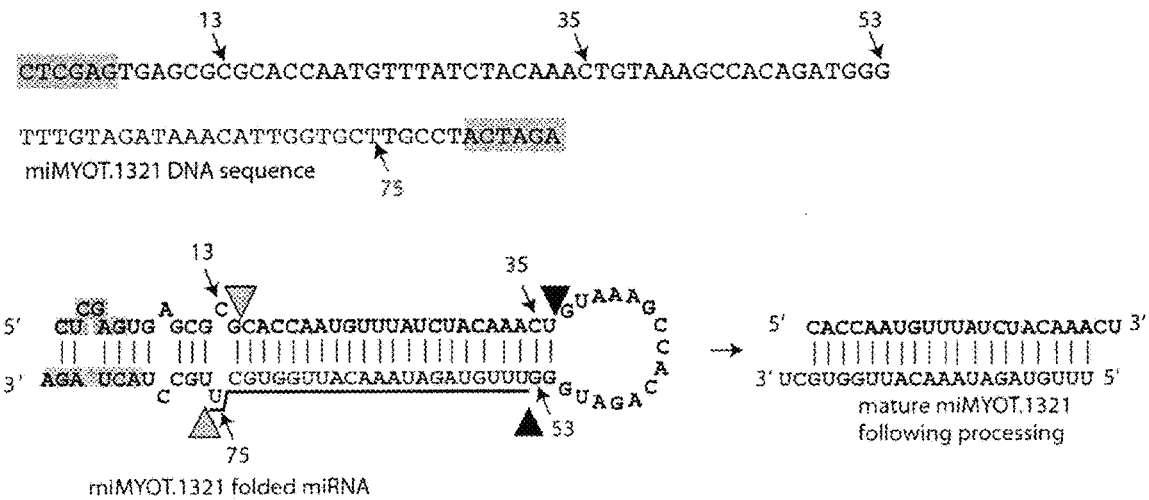
Binds MYOT sequences 1321-1342 from Genbank file: AF144477.1
Binds MYOT sequences 1366-1387 from Genbank file: AF144477.1

L = miMYOT injection  R=miGFP injection

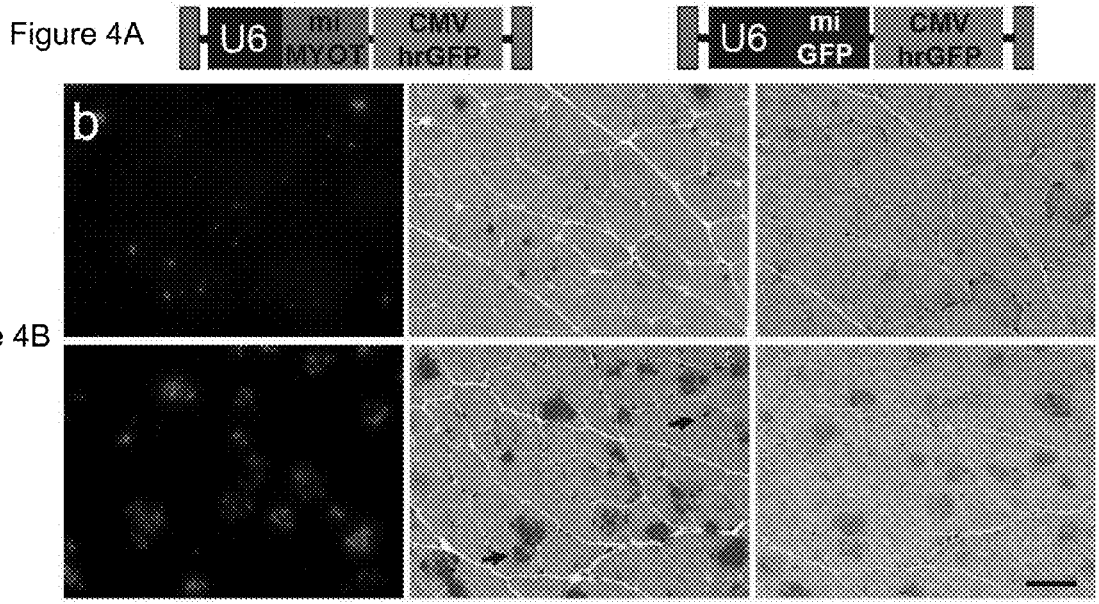
Figure 4A
Figure 4B
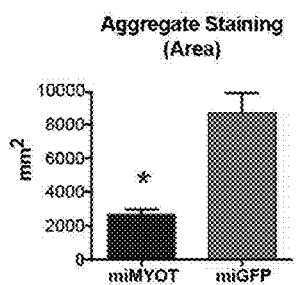
Figure 4C
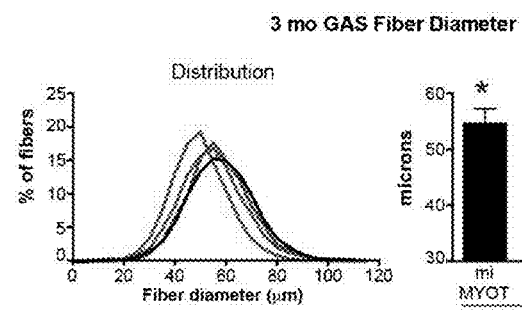
Figure 4D
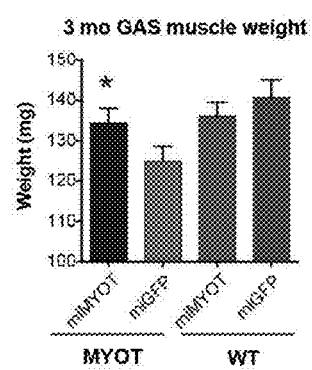
Figure 4E
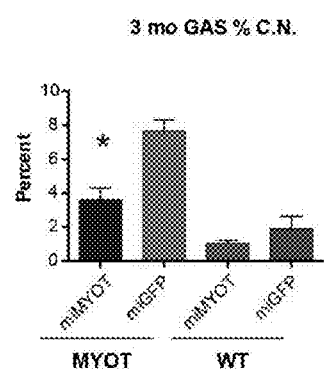
Figure 4F

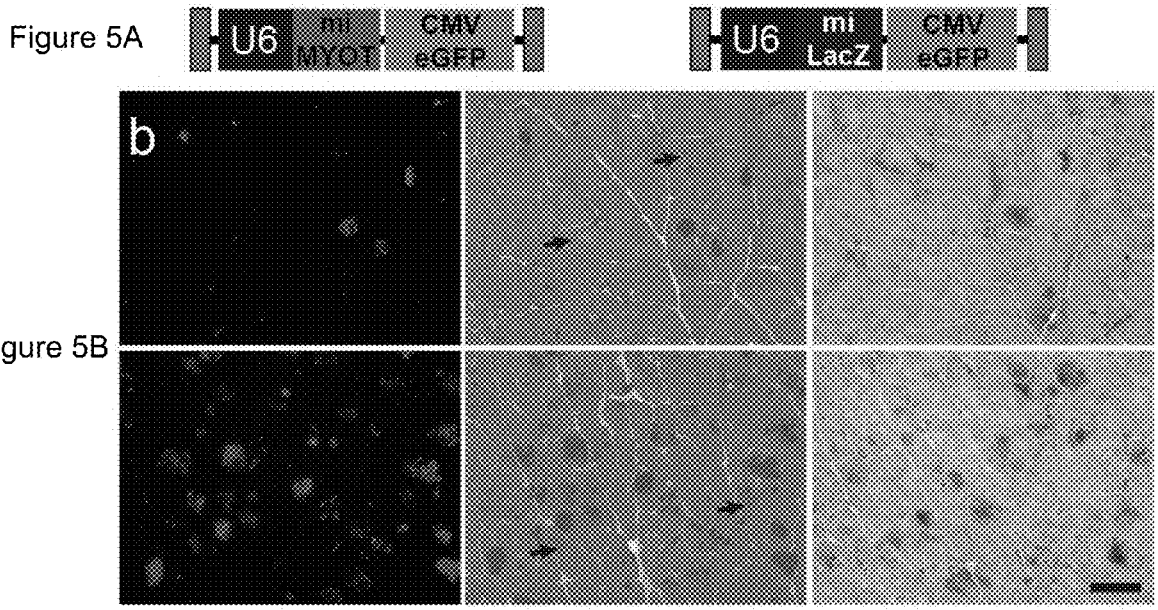
Figure 5A
Figure 5B
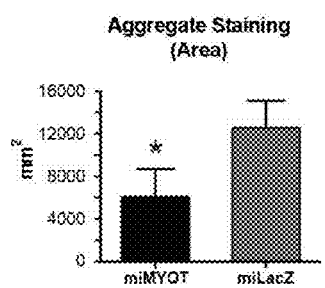
Figure 5C
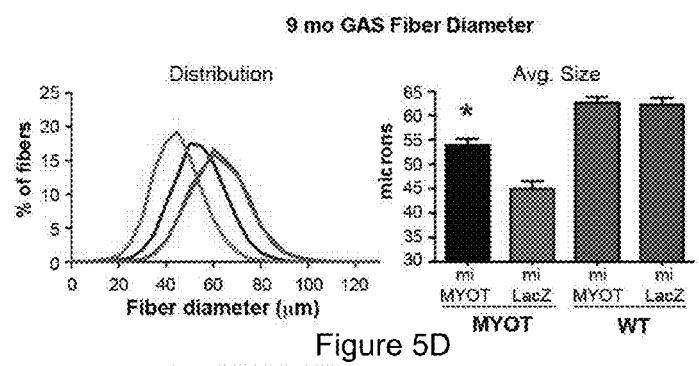
Figure 5D
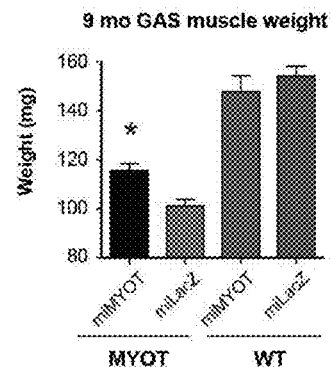
Figure 5E
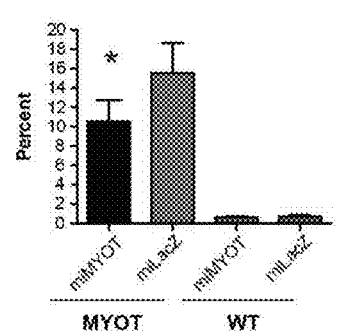
Figure 5F

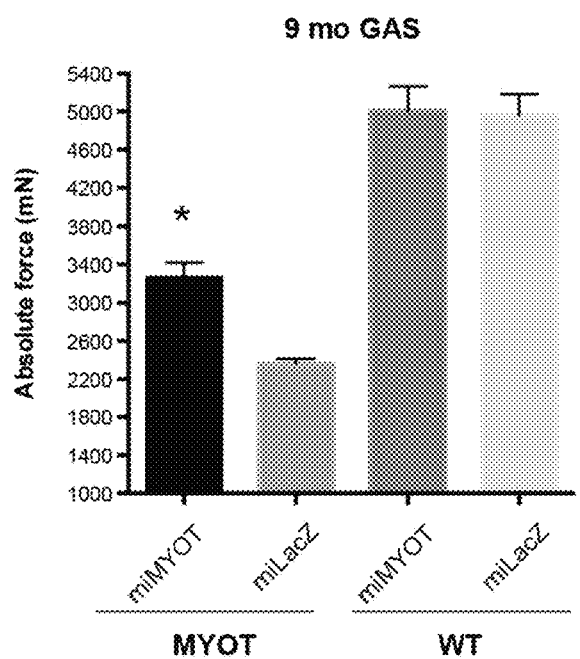
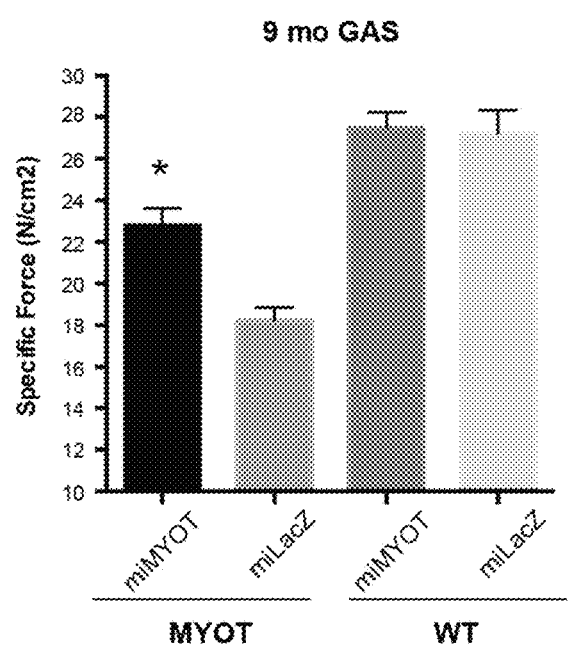
Figure 6A                              Figure 6B

Figure 7
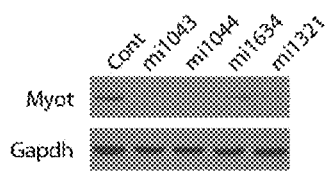
1043 Target site  5' GTGCCAGAGAACATGTCGATTG 3'
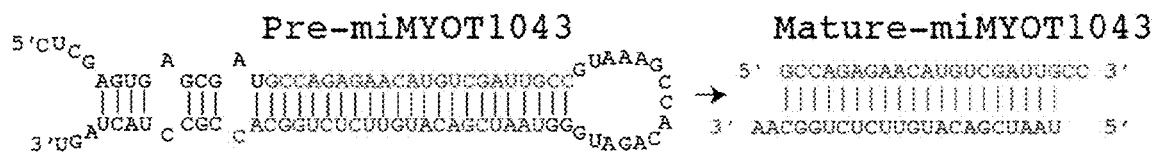
1044 Target site  5'TGCCAGAGAACATGTCGATTGA 3'
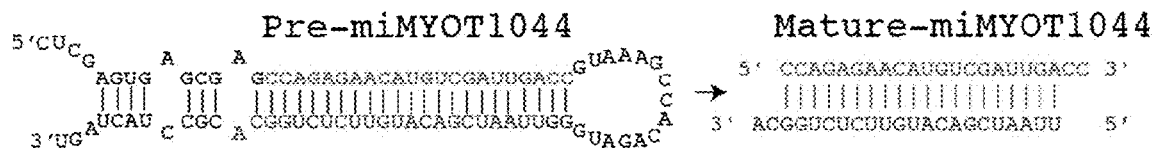
1634 Target site  5' GTGCCAGAGAACATGTCGATTG 3'
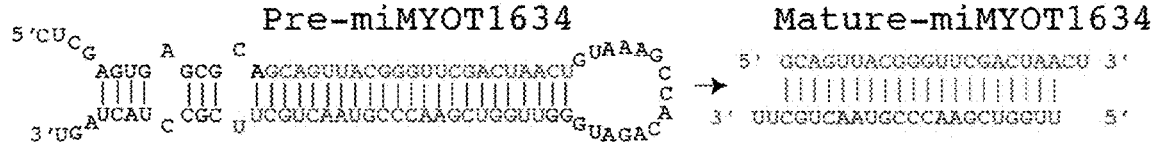
1321 Target site  5' AGCACCAATGTTTATCTACAAA 3'
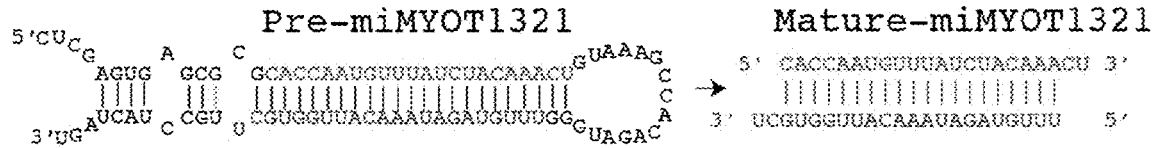

RECOMBINANT VIRUS PRODUCTS AND METHODS FOR INHIBITION OF EXPRESSION OF MYOTILIN

This application is a continuation-in-part of U.S. patent application Ser. No. 14/058,909 filed Jul. 14, 2014, which is in turn a continuation-in-part of International Application No. PCT/US2012/034408 filed Apr. 20, 2012, which claims priority to U.S. Provisional Patent Application No. 61/478,012 filed Apr. 21, 2011, all of which are incorporated by reference herein in their entirety.

FIELD OF THE INVENTION

The present invention relates to RNA interference-based methods for inhibiting the expression of the myotilin gene. Recombinant adeno-associated viruses of the invention deliver DNAs encoding microRNAs that knock down the expression of myotilin. The methods have application in the treatment of muscular dystrophies such as Limb Girdle Muscular Dystrophy Type 1A.

Incorporation by Reference of the Sequence Listing

This application contains, as a separate part of disclosure, a Sequence Listing in computer-readable form (filename: 46208CIP_SeqListing.txt; 1,723,211 bytes-ASCII text file created Sep. 14, 2015) which is incorporated by reference herein in its entirety.

BACKGROUND

Muscular dystrophies (MDs) are a group of genetic diseases. The group is characterized by progressive weakness and degeneration of the skeletal muscles that control movement. Some forms of MD develop in infancy or childhood, while others may not appear until middle age or later. The disorders differ in terms of the distribution and extent of muscle weakness (some forms of MD also affect cardiac muscle), the age of onset, the rate of progression, and the pattern of inheritance.

One group of MDs is the limb girdle group (LGMD) of MDs. LGMDs are rare conditions and they present differently in different people with respect to age of onset, areas of muscle weakness, heart and respiratory involvement, rate of progression and severity. LGMDs can begin in childhood, adolescence, young adulthood or even later. Both genders are affected equally. LGMDs cause weakness in the shoulder and pelvic girdle, with nearby muscles in the upper legs and arms sometimes also weakening with time. Weakness of the legs often appears before that of the arms. Facial muscles are usually unaffected. As the condition progresses, people can have problems with walking and may need to use a wheelchair over time. The involvement of shoulder and arm muscles can lead to difficulty in raising arms over head and in lifting objects. In some types of LGMD, the heart and breathing muscles may be involved.

There are at least nineteen forms of LGMD, and the forms are classified by their associated genetic defects.

| Type | Pattern of Inheritance | Gene or Chromosome |
|---|---|---|
| LGMD1A | Autosomal dominant | Myotilin gene |
| LGMD1B | Autosomal dominant | Lamin A/C gene |
| LGMD1C | Autosomal dominant | Caveolin gene |
| LGMD1D | Autosomal dominant | Chromosome 7 |
| LGMD1E | Autosomal dominant | Desmin gene |
| LGMD1F | Autosomal dominant | Chromosome 7 |
| LGMD1G | Autosomal dominant | Chromosome 4 |
| LGMD2A | Autosomal recessive | Calpain-3 gene |
| LGMD2B | Autosomal recessive | Dysferlin gene |
| LGMD2C | Autosomal recessive | Gamma-sarcoglycan gene |
| LGMD2D | Autosomal recessive | Alpha-sarcoglycan gene |
| LGMD2E | Autosomal recessive | Beta-sarcoglycan gene |
| LGMD2F | Autosomal recessive | Delta-sarcoglycan gene |
| LGMD2G | Autosomal recessive | Telethonin gene |
| LGMD2H | Autosomal recessive | TRIM32 |
| LGMD2I | Autosomal recessive | FKRP gene |
| LGMD2J | Autosomal recessive | Titin gene |
| LGMD2K | Autosomal recessive | POMT1 gene |
| LGMD2L | Autosomal recessive | Fukutin gene |

Specialized tests for LGMD are now available through a national scheme for diagnosis, the National Commissioning Group (NCG).

LGMDIA is caused by gain-of-function missense mutations in the myotilin (MYOT) gene [Hauser et al., Am. J. Hum. Genet, 71:1428-1432 (2002); Hauser et al., Hum. Mol. Genet., 9:2141-2147 (2000); Shalaby et al., J. Neuropathol. Exp. Neurol., 68:701-707 (2009)]. LGMDIA patients develop proximal leg and arm weakness in early adulthood (25 years is mean onset age), which progresses to the distal limb musculature. At the histological level, patients show myofiber degeneration and size variability, fiber splitting, centrally located myonuclei, autophagic vesicles, and replacement of myofibers with fat and fibrotic tissue, which are all common features of muscular dystrophy. Patients with LGMDIA also develop intramuscular myofibrillar protein aggregates, rimmed vacuoles, and severe Z-disc disorganization (called Z-disc streaming), which completely disrupt the sarcomeric structure. A transgenic mouse model, the T57I mouse model, using a mutant human MYOT allele has been developed [Garvey et al., Hum. Mol. Genet. 15:2348-2362 (2006)]. Importantly, T57I mice recapitulate the progressive histological and functional abnormalities associated with LGMD1A, including reduced muscle size, muscle weakness, intramuscular myofibrillar aggregates, Z-disc streaming, and centrally located myonuclei.

The myotilin gene encodes a 57 kDa protein expressed primarily in skeletal and cardiac muscle. Myotilin appears to function as a structural component of the Z-disc, and may therefore contribute to sarcomere assembly, actin filament stabilization, and force transmission in striated muscle. Nevertheless, myotilin is not required for normal muscle development or function, since myotilin null mice are overtly and histologically normal. Specifically, mouse muscles lacking myotilin are indistinguishable from wild type in muscle mass, myofiber size, contractile strength (specific force), and sarcolemmal integrity. Moreover, MYOT null mice develop normally, live a normal life span, and show no histological evidence of muscular dystrophy or Z-disc malformations. Mouse and human myotilin transcripts are expressed in the same tissues, have the same genomic structures, and protein sequences are highly conserved (90% identity; 94% similarity), which indicates a conserved functional.

RNA interference (RNAi) is a mechanism of gene regulation in eukaryotic cells that has been considered for the treatment of various diseases. RNAi refers to post-transcriptional control of gene expression mediated by microRNAs (miRNAs). The miRNAs are small (21-25 nucleotides), noncoding RNAs that share sequence homology and base-pair with cognate messenger RNAs (mRNAs). The interaction between the miRNAs and mRNAs directs cellular gene silencing machinery to prevent the translation of the mRNAs. The RNAi pathway is summarized in Duan (Ed.), Section 7.3 of Chapter 7 in Muscle Gene Therapy, Springer Science+Business Media, LLC (2010). Section 7.4 mentions MYOT RNAi therapy of LGMDIA in mice to demonstrate proof-of-principle for RNAi therapy of dominant muscle disorders.

As an understanding of natural RNAi pathways has developed, researchers have designed artificial miRNAs for use in regulating expression of target genes for treating disease. As described in Section 7.4 of Duan, supra, artificial miRNAs can be transcribed from DNA expression cassettes. The miRNA sequence specific for a target gene is transcribed along with sequences required to direct processing of the miRNA in a cell. Viral vectors such as adeno-associated virus have been used to deliver miRNAs to muscle [Fechner et al., J. Mol. Med., 86:987-997 (2008).

Adeno-associated virus (AAV) is a replication-deficient parvovirus, the single-stranded DNA genome of which is about 4.7 kb in length including 145 nucleotide inverted terminal repeat (ITRs). There are multiple serotypes of AAV. The nucleotide sequences of the genomes of the AAV serotypes are known. For example, the complete genome of AAV-1 is provided in GenBank Accession No. NC_002077; the complete genome of AAV-2 is provided in GenBank Accession No. NC_001401 and Srivastava et al., J. Virol., 45:555-564 {1983); the complete genome of AAV-3 is.provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV-9 genome is provided in Gao et al., J. Virol., 78:6381-6388 (2004); the AAV-10 genome is provided in Mol. Ther., 13 (1): 67-76 (2006); and the AAV-11 genome is provided in Virology, 330 (2): 375-383 (2004). Cis-acting sequences directing viral DNA replication (rep), encapsidation/packaging and host cell chromosome integration are contained within the AAV ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, Current Topics in Microbiology and Immunology, 158:97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is infectious as cloned DNA in plasmids which makes construction of recombinant genomes feasible. Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA. The rep and cap proteins may be provided in trans. Another significant feature of AAV is that it is an extremely stable and hearty virus. It easily withstands the conditions used to inactivate adenovirus (56° C. to 65° C. for several hours), making cold preservation of AAV less critical. AAV may even be lyophilized. Finally, AAV-infected cells are not resistant to superinfection.

There remains a need in the art for a treatment for LGMDIA.

SUMMARY

The present invention provides methods and products for preventing or inhibiting the expression of the MYOT gene. The methods of the invention utilize RNAi to prevent or inhibit the expression of the MYOT gene. The methods involve delivering inhibitory RNAs specific for the MYOT gene to muscle cells. The MYOT inhibitory RNAs contemplated include, but are not limited to, antisense RNAs, small inhibitory RNAs (siRNAs), short hairpin RNAs (shRNAs) or artificial microRNAs (MYOT miRNAs) that inhibit expression of MYOT. Use of the methods and products is indicated, for example, in preventing or treating LGMDIA. Some embodiments of the invention exploit the unique properties of AAV to deliver DNA encoding MYOT inhibitory RNAs to muscle cells. Other embodiments of the invention utilize other vectors (for example, other viral vectors such as adenovirus, retrovirus, lentivirus, equine-associated virus, alphavirus, pox viruses, herpes virus, polio virus, sindbis virus and vaccinia viruses) to deliver polynucleotides encoding MYOT inhibitory RNAs.

In one aspect, the invention provides MYOT miRNAs. In another aspect, the invention provides rAAV encoding the MYOT miRNAs wherein the rAAV lack rep and cap genes. In some embodiments, the MYOT miRNA comprises an miRNA antisense guide strand selected from those set out in SEQ ID NO: 7 through SEQ ID NO: 11266. These sequences comprise antisense "guide" strand sequences of the invention of varying sizes. The antisense guide strand is the strand of the mature miRNA duplex that becomes the RNA component of the RNA induced silencing complex ultimately responsible for sequence-specific gene silencing. See Section 7.3 of Duan, supra. For example, the first antisense guide strand in SEQ ID NO: 7 corresponds to (is the reverse complement of) the 3' end of the myotilin sequence set out in FIG. 1. The second antisense guide strand (SEQ ID NO: 8) is offset one nucleotide from the first and so on. In some embodiments, the GC content of the antisense guide strand is 60% or less, and/or the 5'end of the antisense guide strand is more AU rich while the 3' end is more GC rich. Exemplified MYOT miRNA are encoded by the DNAs set out in SEQ ID NOs: 1, 2, 3, 4, 11286, 11287 and 11288. In some embodiments, rAAV are self-complementary (sc) AAV. In some embodiments, the MYOT miRNA encoding sequences are under the control of a muscle-specific tMCK or CK6 promoter.

In another aspect, the invention provides a composition comprising the rAAV encoding the MYOT miRNA.

In yet another aspect, the invention provides a method of preventing or inhibiting expression of the MYOT gene in a cell comprising contacting the cell with a rAAV encoding an MYOT miRNA, wherein the miRNA is encoded by the DNA set out in SEQ ID NO: 11286, 11287 or 11288, and wherein the rAAV lacks rep and cap genes. Expression of MYOT is inhibited by at least 10, 20, 30, 40, 50, 60, 70, 80, 90, 95 or 99 percent.

In still another aspect, the invention provides a method of delivering DNA encoding the MYOT miRNA set out in SEQ ID NO: 11286, 11287 or 11288 to an animal in need thereof, comprising respectively administering to the animal a rAAV encoding the MYOTmi RNA, wherein the rAAV lacks rep and cap genes.

In yet another aspect, the invention provides a method of preventing or treating a muscular dystrophy (including, but not limited to, LGMD1A) comprising administering a rAAV encoding an MYOT miRNA, wherein the miRNA is encoded by the DNA set out in SEQ ID NO: 11286, 11287 or 11288 and wherein the rAAV lacks rep and cap genes. "Treating" may include ameliorating one or more symptoms of the muscular dystrophy (such as LGMD1A). Molecular, biochemical, histological, and functional endpoints demonstrate the therapeutic efficacy of MYOT miRNAs. Endpoints contemplated by the invention include one or more of: the reduction or elimination of mutant MYOT protein in affected muscles, MYOT gene knockdown, reduction or elimination of (for example, LGMDIA-associated) pathogenic protein aggregates in muscle, increase in myofiber diameters, and improvement in muscle strength.

DETAILED DESCRIPTION

Recombinant AAV genomes of the invention comprise one or more AAV ITRs flanking a polynucleotide encoding, for example, one or more MYOT miRNAs. The polynucleotide is operatively linked to transcriptional control DNA, specifically promoter DNA that is functional in target. Commercial providers such as Ambion Inc. (Austin, TX), Darmacon Inc. (Lafayette, CO), InvivoGen (San Diego, CA), and Molecular Research Laboratories, LLC (Herndon, VA) generate custom inhibitory RNA molecules. In addition, commercial kits are available to produce custom siRNA molecules, such as SILENCER™ siRNA Construction Kit (Ambion Inc., Austin, TX) or psiRNA System (InvivoGen, San Diego, CA). Embodiments include a rAAV genome comprising: the DNA set out in SEQ ID NO: 1 encoding the MYOT miRNA named "miMyoT-1291," the DNA set out in SEQ ID NO: 2 encoding the MYOT miRNA named "miMyoT-1321," the DNA set out in SEQ ID NO: 3 encoding the MYOT miRNA named "miMyoT-1366" or the DNA set out in SEQ ID NO: 4 encoding the MYOT miRNA named "miMyoT-1490." Additional embodiments include, but are not limited to, a rAAV genome comprising: the DNA set out in SEQ ID NO: 11286 encoding the MYOT miRNA named "miMyoT-1043," the DNA set out in SEQ ID NO: 11287 encoding the MYOT miRNA named "miMyoT-1044," and the DNA set out in SEQ ID NO: 11288 encoding the MYOT miRNA named "miMyoT-1634."

The rAAV genomes of the invention lack AAV rep and cap DNA. AAV DNA in the rAAV genomes may be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10 and AAV-11. As noted in the Background section above, the nucleotide sequences of the genomes of various AAV serotypes are known in the art.

DNA plasmids of the invention comprise rAAV genomes of the invention. The DNA plasmids are transferred to cells permissible for infection with a helper virus of AAV (e.g., adenovirus, E1-deleted adenovirus or herpesvirus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10 and AAV-11. Production of pseudotyped rAAV is disclosed in, for example, WO 01/83692 which is incorporated by reference herein in its entirety.

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); Mclaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; 6,258, 595; and McCarty. Mol. Ther., 16 (10): 1648-1656 (2008). The foregoing documents are hereby incorporated by reference in their entirety herein, with particular emphasis on those sections of the documents relating to rAAV production. The production and use of sc rAAV are specifically contemplated.

The invention thus provides packaging cells that produce infectious rAAV. In one embodiment packaging cells may be stably transformed cancer cells such as HeLa cells, 293 cells and PerC.6 cells (a cognate 293 line). In another embodiment, packaging cells are cells that are not transformed cancer cells, such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

Recombinant AAV (i.e., infectious encapsidated rAAV particles) of the invention comprise a rAAV genome. Embodiments include, but are not limited to, the rAAV including a genome encoding the MYOT miRNA set out in SEQ ID NO: 1 (named "AAV-U6-miMyoT-1291"), the rAAV including a genome encoding the MYOT miRNA set out in SEQ ID NO: 2 (named "AAV-U6-miMyoT-1321"), the rAAV including a genome encoding the MYOT miRNA set out in SEQ ID NO: 3 (named "AAV-U6-miMyoT-1366") and the rAAV including a genome encoding the MYOT miRNA set out in SEQ ID NO: 4 (named "AAV-U6-miMyoT-1490"). Additional embodiments include, but are not limited to, the rAAV including a genome encoding the MYOT miRNA set out in SEQ ID NO: 11286 (named "scAAV-tMCK-miMyoT-1043"), the rAAV including a genome encoding the MYOT miRNA set out in SEQ ID NO: 11287 (named "AAV-tMCK-iMyoT-1044") and the rAAV including a genome encoding the MYOT miRNA set out in SEQ ID NO: 11288 (named "AAV-tMCK-miMyoT-1634"). The genomes of the rAAV lack AAV rep and cap DNA, that is, there is no AAV rep or cap DNA between the ITRs of the genomes.

The rAAV may be purified by methods standard in the art such as by column chromatography or cesium chloride gradients. Methods for purifying rAAV vectors from helper virus are known in the art and include methods disclosed in, for example, Clark et al., Hum. Gene Ther., 10 (6): 1031-1039 (1999); Schenpp and Clark, Methods Mol. Med., 69 427-443 (2002); U.S. Pat. No. 6,566,118 and WO 98/09657.

In another embodiment, the invention contemplates compositions comprising rAAV of the present invention. Compositions of the invention comprise rAAV in a pharmaceutically acceptable carrier. The compositions may also comprise other ingredients such as diluents and adjuvants. Acceptable carriers, diluents and adjuvants are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

Titers of rAAV to be administered in methods of the invention will vary depending, for example, on the particular rAAV, the mode of administration, the treatment goal, the individual, and the cell type(s) being targeted, and may be determined by methods standard in the art. Titers of rAAV may range from about $1\times10^6$, about $1\times10^7$, about $1\times10^8$, about $1\times10^9$, about $1\times10^{10}$, about $1\times10^{11}$, about $1\times10^{12}$, about $1\times10^{13}$ to about $1\times10^{14}$ or more DNase resistant particles (DRP) per ml. Dosages may also be expressed in units of viral genomes (vg).

Methods of transducing a target cell with rAAV, in vivo or in vitro, are contemplated by the invention. The in vivo methods comprise the step of administering an effective dose, or effective multiple doses, of a composition comprising a rAAV of the invention to an animal (including a human being) in need thereof. If the dose is administered prior to development of a disorder/disease, the administration is prophylactic. If the dose is administered after the development of a disorder/disease, the administration is therapeutic. In embodiments of the invention, an effective dose is a dose that alleviates (eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival. An example of a disease contemplated for prevention or treatment with methods of the invention is LGMDIA.

Combination therapies are also contemplated by the invention. Combination as used herein includes both simultaneous treatment or sequential treatments. Combinations of methods of the invention with standard medical treatments (e.g., corticosteroids) are specifically contemplated, as are combinations with novel therapies.

Administration of an effective dose of the compositions may be by routes standard in the art including, but not limited to, intramuscular, parenteral, intravenous, oral, buccal, nasal, pulmonary, intracranial, intraosseous, intraocular, rectal, or vaginal. Route(s) of administration and serotype(s) of AAV components of the rAAV (in particular, the AAV ITRs and capsid protein) of the invention may be chosen and/or matched by those skilled in the art taking into account the infection and/or disease state being treated and the target cells/tissue(s) that are to express the MYOT miRNAs.

In particular, actual administration of rAAV of the present invention may be accomplished by using any physical method that will transport the rAAV recombinant vector into the target tissue of an animal. Administration according to the invention includes, but is not limited to, injection into muscle, the bloodstream and/or directly into the liver. Simply resuspending a rAAV in phosphate buffered saline has been demonstrated to be sufficient to provide a vehicle useful for muscle tissue expression, and there are no known restrictions on the carriers or other components that can be co-administered with the rAAV (although compositions that degrade DNA should be avoided in the normal manner with rAAV). Capsid proteins of a rAAV may be modified so that the rAAV is targeted to a particular target tissue of interest such as muscle. See, for example, WO 02/053703, the disclosure of which is incorporated by reference herein. Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The rAAV can be used with any pharmaceutically acceptable carrier for case of administration and handling.

For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of rAAV as a free acid (DNA contains acidic phosphate groups) or a pharmacologically acceptable salt can be prepared in water suitably mixed with a surfactant such as hydroxypropylcellulose. A dispersion of rAAV can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating actions of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

Transduction with rAAV may also be carried out in vitro. In one embodiment, desired target muscle cells are removed from the subject, transduced with rAAV and reintroduced into the subject. Alternatively, syngeneic or xenogeneic muscle cells can be used where those cells will not generate an inappropriate immune response in the subject.

Suitable methods for the transduction and reintroduction of transduced cells into a subject are known in the art. In one embodiment, cells can be transduced in vitro by combining rAAV with muscle cells, e.g., in appropriate media, and screening for those cells harboring the DNA of interest using conventional techniques such as Southern blots and/or PCR, or by using selectable markers. Transduced cells can then be formulated into pharmaceutical compositions, and the composition introduced into the subject by various techniques, such as by intramuscular, intravenous, subcutaneous and intraperitoneal injection, or by injection into smooth and cardiac muscle, using e.g., a catheter.

Transduction of cells with rAAV of the invention results in sustained expression of MYOT miRNAs. The present invention thus provides methods of administering/delivering rAAV which express MYOT miRNAs to an animal, preferably a human being. These methods include transducing tissues (including, but not limited to, tissues such as muscle, organs such as liver and brain, and glands such as salivary glands) with one or more rAAV of the present invention. Transduction may be carried out with gene cassettes comprising tissue specific control elements. For example, one embodiment of the invention provides methods of transducing muscle cells and muscle tissues directed by muscle specific control elements, including, but not limited to, those derived from the actin and myosin gene families, such as from the myoD gene family [See Weintraub et al., Science, 251:761-766 (1991)], the myocyte-specific enhancer binding factor MEF-2 [Cserjesi and Olson, Mol Cell Biol 11:4854-4862 (1991)], control elements derived from the human skeletal actin gene [Muscat et al., Mol Cell Biol, 7:4089-4099 (1987)], the cardiac actin gene, muscle creatine kinase sequence elements [See Johnson et al., Mol Cell Biol, 9:3393-3399 (1989)] and the murine creatine kinase enhancer (mCK) element, control elements derived from the skeletal fast-twitch troponin C gene, the slow-twitch cardiac troponin C gene and the slow-twitch troponin I gene: hypozia-inducible nuclear factors [Semenza et al., Proc Natl Acad Sci USA, 88:5680-5684 (1991)], steroid-inducible elements and promoters including the glucocorticoid response element (GRE) [See Mader and White, Proc. Natl. Acad. Sci. USA, 90:5603-5607 (1993)]. the tMCK promoter [see Wang et al., Gene Therapy, 15:1489-1499 (2008)], the CK6 promoter [see Wang et al., supra] and other control elements.

Muscle tissue is an attractive target for in vivo DNA delivery, because it is not a vital organ and is easy to access. The invention contemplates sustained expression of miRNAs from transduced myofibers.

By "muscle cell" or "muscle tissue" is meant a cell or group of cells derived from muscle of any kind (for example, skeletal muscle and smooth muscle, e.g. from the digestive tract, urinary bladder, blood vessels or cardiac tissue). Such muscle cells may be differentiated or undifferentiated, such as myoblasts, myocytes, myotubes, cardiomyocytes and cardiomyoblasts.

The term "transduction" is used to refer to the administration/delivery of MYOT miRNAs to a recipient cell either in vivo or in vitro, via a replication-deficient rAAV of the invention resulting in expression of a MYOT miRNA by the recipient cell.

Thus, the invention provides methods of administering an effective dose (or doses, administered essentially simultaneously or doses given at intervals) of rAAV that encode MYOT miRNAs to a patient in need thereof.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 1 shows target sites in the myotilin sequence (SEQ ID NO: 11266) for exemplified miRNAs.

FIG. 2 sets out sequences of two MYOT-targeted miRNAs. In each panel, the top sequences indicate the DNA templates from which each respective miRNA is transcribed. In the top panel, the DNA template miMYOT.1321 is SEQ ID NO: 2. In the bottom panel, the DNA template miMYOT.1366 is SEQ ID NO: 3. The folded miRNA transcripts are shown as hairpin structures. The miMYOT.1321 folded miRNA is SEQ ID NO: 11268. The miMYOT.1366 folded miRNA is SEQ ID NO: 11271. The mature miMYO.1321 (SEQ ID NO: 11270 which pairs with SEQ ID NO: 11269 in the figure) and miDUX4.1366 (SEQ ID NO: 11273 which pairs with SEQ ID NO: 11272 in the figure) sequences arise following processing in target cells by host miRNA processing machinery (including Drosha, DGCR8, Dicer, and Exportin-5). Sequences shaded in gray indicate sites used for cloning each miRNA into the U6T6 vector. The nucleotides corresponding to the mature miRNA antisense guide strand that ultimately helps catalyze cleavage of the MYOT target mRNA are underlined in the miRNA hairpin portions of this diagram. The gray and black arrowheads indicate Drosha—and Dicer-catalyzed cleavage sites, respectively. The numbers 13, 35, 53, and 75 are provided for orientation. The sequences between (and including) positions 35-53 are derived from the natural human mir-30a sequence, except the A at position 39, which is a G is the normal mir-30a sequence. This was changed to an A to facilitate folding of the miRNA loop, based on in silico RNA folding models. The base of the stem (5' of position 13 and 3' of position 75) is also derived from mir-30a structure and sequence with some modifications depending on the primary sequence of the guide strand. Specifically, the nucleotide at position 13 can vary to help facilitate a required mismatched between the position 13 and 75 nucleotides. This bulged structure is hypothesized to facilitate proper Drosha cleavage.

FIG. 3 shows the effect of MYOT-targeted miRNAs in LGMDIA mice expressing mutant myotilin (MYOT).

FIG. 4 shows AAV.miMYO.1321 (labeled miMYOT in the figure) improves histopathology and muscle weight in 3-mo old TgT57I mice. FIG. 4A. AAV vectors used in 3-mo studies. The miMYOT and control miGFP RNAs are expressed from the mouse U6 promoter. Both vectors contain a CMV.hrGFP reporter gene cassette. Red rectangles indicated AAV inverted terminal repeats (ITRs). FIG. 4B. Representative serial sections from T571 mice injected with AAV.miMYOT (top panels) or AAV.miGFP (bottom panels) controls show reductions in MYOT-seeded protein aggregates. Red spots are protein aggregates stained by immunofluorescence with MYOT antibodies. Middle panels show overlay with H&E-stained serial sections. Arrows indicate fibers containing centrally-located myonuclei. Right panels, aggregates are visible as dark blue spots within the myofiber in serial sections stained with Gomori's Trichrome, while nuclei are purple. Scale bar, 50 µm. Images shown are representative of 8 independently injected animals per virus. FIG. 4C. Quantification of aggregate staining 3 months after injecting TgT57I GAS muscles with AAV.miMYOT or AAV.miGFP. MYOT knockdown significantly reduced the average area of MYOT-positive aggregates by 69% (N=5 muscles per group; 5 randomly sampled fields per muscle; paired t-test, p=0.0069; errors bars represent s.c.m.) FIG. 4D. Graphs show the distribution and average size of TgT571 and wild-type (WT) muscles treated with AAV.miMYOT or AAV.miGFP controls, 3 months post-injection. MYOT knockdown in TgT571 muscles significantly improved myofiber diameter by 4.9 microns (54.8 µm versus 49.9 µm in control-treated TgT57I mice; t-test, p=0.047). WT fiber diameters were 57 and 57.7 microns, in miMYOT—and miGFP-treated animals, respectively. N=5 muscles per group; 5 randomly selected fields per muscle; an average of 1,205 fibers counted per wild-type animals and 1,433 fibers per TgT57I animal). (c) AAV.miMYOT significantly improved GAS muscle weight by 9.5 mg in 3-mo old TgT57I mice (t-test, p<0.001; N=12 muscles per group). AAV.miMYOT treated muscles averaged 134.4 mg in weight versus 124.9 mg in AAV.miGFP-treated animals; WT controls: miMYOT, 136.0 mg; miGFP, 140.8 mg). (f) The mild degeneration-regeneration effects in TgT571 muscles, as indicated by the presence of myofibers with centrally-located nuclei, were significantly improved 2.1-fold with AAV.miMYOT treatment compared to controls (t-test, p=0.0004). Both group of TgT57I mice were still significantly different from respective WT controls (t-test, p<0.006). *, indicates significant difference between miMYOT—and miGFP-treated TgT57I animals. Wild-type animals were not significantly different from one another by all measures, regardless of treatment.

FIG. 5 shows shows AAV.miMYO.1321 (labeled miMYOT in the figure) mproves histopathology and muscle weight in 9-mo old TgT57I mice. FIG. 5A. AAV vectors used in 9-mo studies. The miMYOT and control miLacZ RNAs are expressed from the mouse U6 promoter. Both vectors contain a CMV.eGFP reporter gene cassette. Red rectangles indicated AAV inverted terminal repeats (ITRs). FIG. 5B. Representative serial sections from T57I mice injected with AAV.miMYOT (top panels) or AAV.miLacZ (bottom panels) controls show reductions in MYOT-seeded protein aggregates. Red spots are protein aggregates stained by immunofluorescence with MYOT antibodies. Middle panels show overlay with H&E-stained serial sections. Arrows indicate fibers containing centrally-located myonuclei. Right panels, aggregates are visible as dark blue spots within the myofiber in serial sections stained with Gomori's Trichrome, while nuclei are purple. Scale bar, 50 µm. Images shown are representative of 8 independently injected animals per virus. FIG. 5C. Quantification of aggregate staining 9 months after injecting TgT57I GAS muscles with AAV.miMYOT or AAV.miLacZ. MYOT knockdown significantly reduced the average area of MYOT-positive aggregates by 52% (N=5 muscles per group; 5 randomly sampled fields per muscle; paired t-test, p=0.0085; errors bars represent s.c.m.) FIG. 5D. Graphs show the distribution and average size of TgT571 and wild-type (WT) muscles treated with AAV.miMYOT or AAV.miLacZ controls, 9 months post-injection. MYOT knockdown in TgT571 muscles significantly improved myofiber diameter by 9.1 microns (54 µm versus 44.9 µm in control-treated TgT57I mice; t-test, p=0.0006). WT fiber diameters were 62.5 and 62.2 microns, in miMYOT—and miLacZ-treated animals, respectively. These values were significantly larger than either TgT571 group (p<0.001, t-test). N=5 muscles per group; 5 randomly selected fields per muscle; an average of 993 fibers counted per wild-type animals and 1,554 fibers per TgT57I animal). (c) AAV.miMYOT significantly improved GAS muscle weight by 15 mg in 9-mo old TgT571 mice (t-test, p=0.002; N=8 muscles per group). AAV.miMYOT treated muscles averaged 116 mg in weight versus 101 mg in AAV.miLacZ-treated animals; WT controls: miMYOT, 148 mg; miGFP, 154 mg). (f) The mild degeneration-regeneration effects in TgT571 muscles, as indicated by the presence of myofibers with centrally-located nuclei, were significantly improved 2.1-fold with AAV.miMYOT treatment compared to controls (t-test, p=0.0004). Both group of TgT57I mice were still significantly different from respective WT controls (t-test, p<0.0001). *, indicates significant difference between miMYOT—and miLacZ-treated TgT57I animals. Wild-type animals were not significantly different from one another by all measures, regardless of treatment.

FIG. 6 shows AAV.miMYO.1321 (labeled miMYOT in the figure) significantly improves whole muscle strength in TgT57I mice 9 months after treatment. AAV.miMYOT-treated TgT57I GAS muscles showed statistically significant 38% and 25% improvements in absolute force (FIG. 6A) and specific force (FIG. 6B) compared to AAV.miLacZ-treated controls (N=6-8 legs; p=0.02 for (a) and p=0.0009 for (b), t-test). Both TgT57I groups were significantly weaker than their WT counterparts (p<0.0001, t-test), while wild-type groups were not significantly different from one another.

FIG. 7 shows precursor and mature forms of miRNAs miMYOT-1043 (SEQ ID NO: 11286), miMYOT-1044 (SEQ ID NO: 11287), miMYOT-1634 (SEQ ID NO: 11288) and miMYOT-1321 (SEQ ID NO: 2), as well as a Western blot showing each miRNA reduces MyoT protein in vitro to levels similar to the miMYOT-1321 miRNA.

EXAMPLES

Figure 3A:
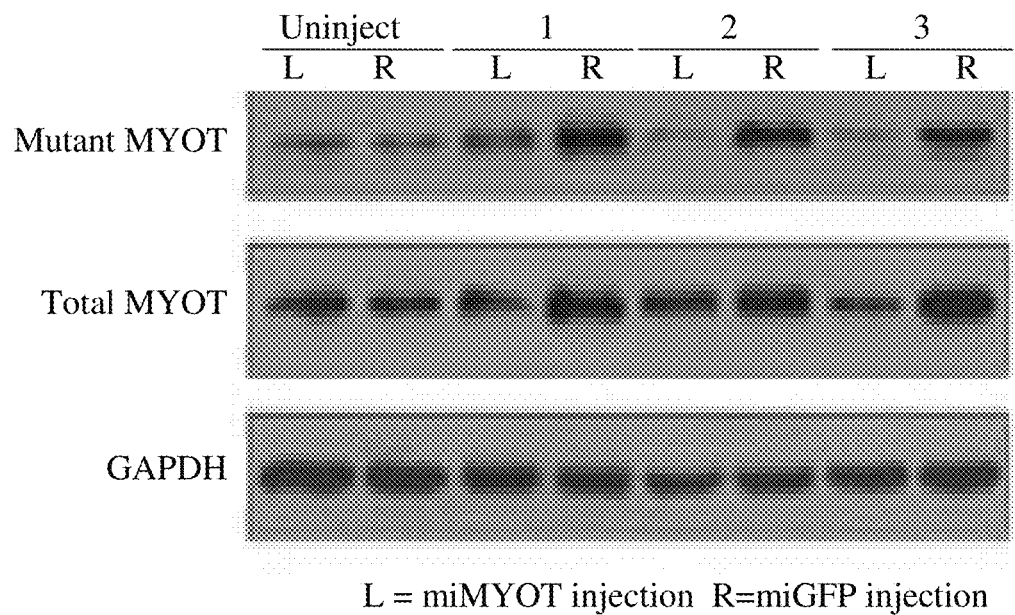
FIG. 3A is a Western blot showing knockdown of mutant myotilin expression is muscle extracts from three-month old LGMDIA mice, where Left (L)=miMYOT treatment side and Right (R)=miGFP control treated side.

Aspects and embodiments of the invention are illustrated by the following examples. Example 1 describes miRNAs specific for the MYOT gene. Example 2 describes the effect of the miRNAs on the expression of MYOT as measured by real-time PCR. Example 3 describes rAAV encoding the miRNAs. Example 4 describes the effect of the U6T6 expressing the miRNAs on the expression of MYOT as measured by Western blot. Example 5 describes delivery of MYOT miRNA to newborn mice. Example 6 describes delivery of MYOT miRNA to adult mice. Example 7 describes dose escalation and self-complementary AAV (scAAV) vectors. Example 8 describes miRNAs with base pair mismatches.

Example 1

MicroRNAs Specific for the MYOT Gene

Six DNAs encoding miRNAs specific for the MYOT gene were generated by PCR. The PCR primers used had the following sequences.

```
Primer 775 (miMyoT-592-Forward)
                                    (SEQ ID NO: 11274)
AAAACTCGAGTGAGCGACCTGATTACAATAGCAGTAAACTGTAAAGCCAC

AGATGGG

Primer 776 (miMyoT-592-Reverse)
                                    (SEQ ID NO: 11275)
TTTTACTAGTAGGCAGCCTGATTACAATAGCAGTAAACCCATCTGTGGCT

TTACAG

Primer 777 (miMyoT-1291-Forward)
                                    (SEQ ID NO: 11276)
AAAACTCGAGTGAGCGACTGGATGTCCTTGCAAAAGAACTGTAAAGCCAC

AGATGGG

Primer 778 (miMyoT-1291-Reverse)
                                    (SEQ ID NO: 11277)
TTTTACTAGTAGGCAGCTGGATGTCCTTGCAAAAGAACCCATCTGTGGCT

TTACAG
```

```
-continued
Primer 779 (miMyoT-1321-Forward)
                                    (SEQ ID NO: 11278)
AAAACTCGAGTGAGCGCGCACCAATGTTTATCTACAAACTGTAAAGCCAC

AGATGGG

Primer 780 (miMyoT-1321-Reverse)
                                    (SEQ ID NO: 11279)
TTTTACTAGTAGGCAAGCACCAATGTTTATCTACAAACCCATCTGTGGCT

TTACAG

Primer 781 (miMyoT-1366-Forward)
                                    (SEQ ID NO: 11280)
AAAACTCGAGTGAGCGAGGAGATTCAGTGAAACTAGAACTGTAAAGCCAC

AGATGGG

Primer 782 (miMyoT-1366-Reverse)
                                    (SEQ ID NO: 11281)
TTTTACTAGTAGGCAGGGAGATTCAGTGAAACTAGAACCCATCTGTGGCT

TTACAG

Primer 783 (miMyoT-1490-Forward)
                                    (SEQ ID NO: 11282)
AAAACTCGAGTGAGCGCGAAGAGTTACTTTACTGATAACTGTAAAGCCAC

AGATGGG

Primer 784 (miMyoT-1490-Reverse)
                                    (SEQ ID NO: 11283)
TTTTACTAGTAGGCAGGAAGAGTTACTTTACTGATAACCCATCTGTGGCT

TTACAG

Primer 785 (miMyoT-1603-Forward)
                                    (SEQ ID NO: 11284)
AAAACTCGAGTGAGCGAGCACGTCCAAACCAAACTCTTCTGTAAAGCCAC

AGATGGG

Primer 786 (miMyoT-1603-Reverse)
                                    (SEQ ID NO: 11285)
TTTTACTAGTAGGCAGGCACGTCCAAACCAAACTCTTCCCATCTGTGGCT

TTACAG
```

DNA encoding a miRNA designated miMyoT-592 was generated using primers 775 and 776. DNA encoding miRNA designated miMyoT-1291 was generated using primers 777 and 778. DNA encoding miRNA designated miMyoT-1321 was generated using primers 779 and 780. DNA encoding miRNA designated miMyoT-1366 was generated using primers 781 and 782. DNA encoding miRNA designated miMyoT-1490 was generated using primers 783 and 784. DNA encoding miRNA designated miMyoT-1603 was generated using primers 785 and 786. The DNAs are set out below, wherein the number in the names indicates the 5' target nucleotide in the myotylin sequence (SEQ ID NO: 11267). See FIG. 1 where the target sequences for the miRNAs in the myotilin sequence are underlined.

```
miMyoT-592
                                       (SEQ ID NO: 5)
CTCGAGTGAGCGACCTGATTACAATAGCAGTAAACTGTAAAGCCACAGAT

GGGTTTACTGCTATTGTAATCAGGCTGCCTACTAGA miMyoT-1291
                                       (SEQ ID NO: 1)
CTCGAGTGAGCGACTGGATGTCCTTGCAAAAGAACTGTAAAGCCACAGAT

GGGTTATTTTGCAAGGACATCCAGCTGCCTACTAGA
```

-continued miMyoT-1321
(SEQ ID NO: 2)
CTCGAGTGAGCGCGCACCAATGTTTATCTACAAACTGTAAAGCCACAGAT

GGGTTTGTAGATAAACATTGGTGCTTGCCTACTAGA miMyoT-1366
(SEQ ID NO: 3)
CTCGAGTGAGCGAGGAGATTCAGTGAAACTAGAACTGTAAAGCCACAGAT

GGGTTCTAGTTTCACTGAATCTCCCTGCCTACTAGA miMyoT-1490
(SEQ ID NO: 4)
CTCGAGTGAGCGCGAAGAGTTACTTTACTGATAACTGTAAAGCCACAGAT

GGGTTATCAGTAAAGTAACTCTTCCTGCCTACTAGA miMyoT-1603
(SEQ ID NO: 6)
CTCGAGTGAGCGAGCACGTCCAAACCAAACTCTTCTGTAAAGCCACAGAT

GGGAAGAGTTTGGTTTACGTGCCTGCCTACTAGA

FIG. 2 shows the DNA templates miMyoT.1321 and miMyoT.1366 and their corresponding folded and mature miRNAs.

One µg of each primer was added to a 1 cycle primer extension reaction: 95° C. for 5 min.; 94° C. for 2 min.; 52° C. for 1 min.; 72° C. for 15 min.; and then holding at 4° C. The PCR products were cleaned up with the Qiagen QIAquick PCR Purification kit before being digested overnight with XhoI and SpeI restriction enzymes. The digestion product was then run on a 1.5% TBE gel and the band excised and purified using the Qiagen QIAquick Gel Extraction Kit.

The PCR products were ligated to a U6T6 vector (via XhoI and XbaI) overnight. This vector contains a mouse U6 promoter and an RNA polymerase III termination signal (6 thymidine nucleotides). miRNAs are cloned into XhoI+XbaI restriction sites located between the 3' end of the U6 promoter and the termination signal (SpeI on the 3' end of the DNA template for each miRNA has complementary cohesive ends with the XbaI site). The ligation product was transformed into chemically competent E-coli cells with a 42° C. heat shock and incubated at 37° C. shaking for 1 hour before being plated on kanamycin selection plates. The colonies were allowed to grow overnight at 37°. The following day they were mini-prepped and sequenced for accuracy.

Example 2

Real-Time PCR Reaction for Effect of Expression of MYOT miRNAs

Expression of the MYOT target sequence in the presence of the MYOT miRNAs was assayed. A lipofectamine 2000 transfection was done in C2C12 cells in a 12-well, whitewalled assay plate. 52,000 cells were transfected with 100 ng of AAV-CMV-mutMyoT and 1500 ng of one of the U6T6 vectors described in Example I containing miRNA-encoding DNA. The assay was performed 48 hours later.

The media was removed from the cells and 1 µl of Trizol was added per well. Then the cells were resuspended and the lysates were transferred to 1.5 ml EP tubes. Samples were incubated at room temperature for 5 min and 200 µl chloroform was added. The tubes were shaken vigorously for 15 sec, incubated at room temperature for 3 min and centrifuged at 12,000 g for 15 min at 4° C. Then the aqueous phase was transferred to a fresh tube and 0.5 ml isopropyl alcohol was added. The samples were incubated at room temperature for 10 min and centrifuged at 12,000 g for 10 min at 4° C. The RNA pallet was washed once with 1 ml 75% ethanol and aired dry. 20 µl of RNase-Free water was added to dissolve the pellet and the concentration/purification were measured by Nano-drop. 1.5 µg total RNA was added to cDNA generation reaction: 5° C. for 10 min.; 37° C. for 120 min.; 85° C. for 5 sec and then holding at 4° C. The cDNA products were diluted at 1:10 and 4.5 µl was added to real-time PCR reaction. Human Myotilin was used to check the expression of the MYOT and the relative expression was normalized to mouse GAPDH expression.

U6T6-miMyoT-592 (SEQ ID NO: 5) showed higher expression of MYOT than U6T6-miGFP control. U6T6-miMyoT-1291 (SEQ ID NO: 1) reduced the expression of MYOT to 60%, U6T6-miMyoT-1321 (SEQ ID NO: 2) reduced the expression of MYOT to 19%, U6T6-miMyoT-1366 (SEQ ID NO: 3) reduced the expression of MYOT to 41.7%, U6T6-miMyoT-1490 (SEQ ID NO: 4) reduced the expression of MYOT to 55.3%, U6T6-miMyoT-1603 (SEQ ID NO: 6) reduced the expression of MYOT to 34.9%, when compared to U6T6-miGFP control.

Example 3

Production of rAAV Encoding MYOT MicroRNAs

The U6-miMYOT DNAs were cut from U6T6-miMYOT constructs at EcoRI sites and then respectively cloned into AAV6-hrGFPs to generate rAAV-U6-miMyoT vectors. These rAAV vectors express miRNA and hrGFP Example 4

Western Blot Assay for Effect of
Expression of MYOT miRNAs from U6T6 Vectors and rAAV The effect of expression of MYOT miRNAs from the U6T6 vectors described in Example 1 and the rAAV described in Example 3 was assayed by Western blot.

One day before transfection, 293 cells were plated in a 24-well plate at 1.5×10⁵ cells/well. The cells were then transfected with U6T6-miMyoT (592, 1291, 1321, 1366, 1490 or 1603) using Lipofectamine 2000 (Invitrogen, Cat. No. 11668-019).

Forty-eight hours after transfection, cells were collected and washed with cold PBS once. Seventy µl lysis buffer (137 mM NaCl, 10 mM Tris pH=7.4, 1% NP40) were then added. The cells were resuspended completely and incubated on ice for 30 min. The samples were centrifuged for 20 min at 13,000 rpm at 4° C. and the supernatant was collected. The cell lysate was diluted 5-fold for the Lowry protein concentration assay (Bio-Rad Dc Protein Assay Reagent A, B, S; Cat. No. 500-0113, 500-0114, 500-115). Twenty µg of each sample was taken and 2× sample buffer (100 mM Tris pH=6.8, 100 mM DTT, 10% glycerol, 2% SDS. 0.006% bromophenol blue) was added. The samples were boiled for 10 min and then put on ice.

The samples were loaded onto a 10% polyacrylamide gel (based on 37.5:1 acrylamide: bis acrylamide ratio, Bio-Rad, Cat. No. 161-0158). 15 µg on a gel for each sample. Proteins were transferred to PVDF membranes at 15 V for 1 h using semi-dry transfer (Trans-Blot SD Semi-Dry Transfer Cell, Bio-Rad, Cat. No. 170-3940). The blots were placed into blocking buffer (5% non-fat dry milk, 30 mM Tris pH=7.5, 150 mM NaCl, 0.05% Tween-20) and agitated for 1 h at room temperature. The blocking buffer was decanted and anti-myotilin primary antibody solution (rabbit polyclonal generated by Bethyl Laboratories using a peptide corresponding to myotilin residues 473-488) was added and incubated with agitation overnight at 4° C. The membranes were then washed for 30 min, changing the wash buffer (150 mM NaCl, 30 mM Tris pH=7.5, 0.05% Tween-20) every 10 min. Peroxidase-conjugated Goat Anti-Mouse Antibody (Jackson ImmunoReserch, Cat. No. 115-035-146, 1: 100, 000) was added and incubated at room temperature for 2 h. The membranes were then washed for 30 min, changing the wash buffer every 10 min. The blots were placed in chemiluminescent working solution (Immobilon Western Chemiluminescent HRP Substrate, Millipore, Cat. No. WBKLS0500), incubated with agitation for 5 min at room temperature, and then exposed to X-ray film.

The membranes were washed for 20 min, changing the wash buffer every 10 min. Next, stripping buffer (2% SDS, 62.5 mM Tris pH=6.7, 100 mM b-ME) was added to the blots and incubated at 50° C. for 30 min. The membranes were washed again for 30 min, changing the wash buffer every 10 min. Then, the membranes were blocked again and re-probed with Anti-GAPDH primary antibody solution (Chemicon, Cat. No. MAB374, 1:200) and peroxidase-conjugated Goat Anti-Mouse Antibody (Jackson ImmunoReserch, Cat. No. 115-035-146, 1:100,000) was used as secondary antibody.

The film was scanned and the density ratio of MYOT to GAPDH was calculated. Compared to U6T6-miGFP control, the expression of MYOT was higher (1.08) in samples of U6T6-miMyoT-592 (SEQ ID NO: 5) and the the expression of MYOT was reduced to 78.9% by U6T6-miMyoT-1291 (SEQ ID NO: 1), 50.2% by U6T6-miMyoT-1321 (SEQ ID NO: 2), 60.2% by U6T6-miMyoT-1366 (SEQ ID NO: 3), 76.2% by U6T6-miMyoT-1490 (SEQ ID NO: 4), 87% by U6T6-miMyoT-1603 (SEQ ID NO: 6). U6T6-miMYOT-1321 most effectively knocked down myotilin expression both in the real-time PCR and western-blot experiments. The knockdown effect by AAV-miMyoT-1321 was also confirmed by western-blot experiment.

Example 5

Delivery to Newborn Mice

The PCR genotype of newborn pups was determined to identify female WT or T57I MYOT mice (using human MYOT primers and Y chromosome primers). Bilateral intramuscular injections of $5 \times 10^{10}$ AAV6.miMYOT-1321 or control AAV6.miGFP particles per leg in 1-2 day old mice were sufficient to saturate the lower limb musculature.

Phenotypic correction was then determined initially by histological analyses. Specifically, 3 months after viral delivery, muscles were harvested and cryopreserved. Ten micron serial cryosections were cut and stained with antibodies to detect myotilin-positive protein aggregates in T57I myofibers. AAV6.miMYOT-1321 muscles had significantly reduced numbers of aggregates per section compared to AAV6.miGFP or untreated controls. In addition, when AAV6.miMYOT-132-treated muscles did show occasional aggregates, they were significantly smaller than those seen in control-treated or untreated T57I animals. AAV6.miMYOT-132 treatment also improved muscle size deficits relative to the control treatment.

Figure 3B:
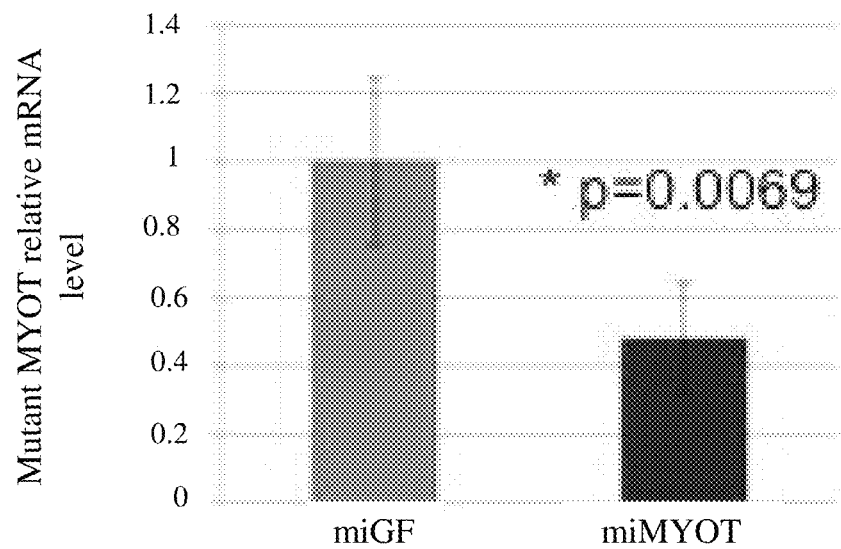
FIG. 3B shows real-time PCR results confirming the Western data.

MYOT knockdown was confirmed by Western blot and real-time PCR as shown in FIG. 3. The AAV delivered miMYOT-1321 significantly reduced mutant MYOT protein (FIG. 3A) and mRNA (FIG. 3B) in the muscles.

These results support therapeutic efficacy. Continuing experiments include determining the functional effects of MYOT knockdown in whole muscles by measuring EDL specific force.

Example 6

Delivery to Adult Mice

The PCR genotype of weanlings is determined, and 3-month old or 9-month old mice which have significant pre-existing LGMDIA-associated pathology are chosen for treatment. $5 \times 10^{10}$ AAV6 vectors are delivered to lower limb musculature by isolated leg perfusion. Phenotypic correction (including hindlimb grip strength, gross muscle parameters and EDL specific force are then measured using various methods over the following months.

Male P1 or P2 mice were injected in the lower limbs with $5 \times 10^{10}$ DNAse resistant particles AAV6.miMYOT.1321 or control AAV6.miGFP particles per leg. Muscles were harvested for analysis at 3 months and 9 months of age. All mouse protocols were approved by the Institutional Animal Care and Use Committee (IACUC) at The Research Institute of Nationwide Children's Hospital.

Imaging and histology. In vivo AAV transduction was determined by GFP epifluorescence using a fluorescent dissecting microscope (MZ16FA, Leica, Wetzlar, Germany). Dissected muscles were placed in O.C.T. Compound (Tissue-Tek, Torrance, CA) and frozen in liquid nitrogen-cooled 2-methylbutane. The blocks were cut onto slides as 10 μm cryosections, and stained with hematoxylin and eosin (H&E; following standard protocols), or anti-MYOT polyclonal antibodies. For MYOT immunohistochemistry, cryosections were fixed in methanol and blocked in GFTP+buffer (5% normal goat serum, 0.1% pig gelatin, 1% BSA, 0.2% Triton X-100, in phosphate-buffered saline). Slides were incubated overnight at 4° C. with MYOT primary antibody (1:400), and then with AlexaFluor-594 conjugated goat anti-rabbit secondary antibodies (1:500; 1 hour at RT; Molecular Probes, Carlsbad, CA). Images were taken from mouse tissue harvested from 3-and 9-month old male mice. Muscle cross-sectional fiber diameters and percentage of myofibers with centrally-located nuclei were determined as previously described from five different animals per group (five fields per leg).

Contractile measurements of gastrocnemius muscle. Mice were anesthetized with intraperitoneal injection of Avertin (250 mg/kg) with supplemental injections given to maintain an adequate level of anesthesia during the whole procedure. The gastrocnemius muscle was exposed and the distal tendon was isolated and cut. The exposed muscle and tendon were kept moist by periodic applications of isotonic saline. Knot was tied at the proximal end of the tendon and the mouse was placed on a heated platform maintained at 37° C. The tendon was tied securely to the lever arm of a servo-motor (6650LR, Cambridge Technology) via the suture ends. The muscle was then stimulated with 0.2 ms pulses via the peroneal nerve using platinum electrodes. Stimulation voltage and muscle length were adjusted for maximum isometric twitch force (Pt). The muscle was stimulated at increasing frequencies until a maximum force (Po) was reached at optimal muscle length (Lo). Optimum fiber length (Lf) was determined by multiplying Lo by the gastrocnemius Lf/Lo ratio of 0.45. Total fiber CSA was calculated by dividing the muscle mass (mg) by the product of muscle fiber length (mm) and the density of mammalian skeletal muscle, 1.06 g/cm². Specific Po (N/cm2) was calculated by dividing Po by total fiber CSA for each muscle.

Immediately after muscle mass was measured, muscles were coated in tissue freezing medium (Triangle Biomedical Sciences, Durham, NC), frozen in isopentane cooled by dry ice, and stored at −80° C. until needed.

EDL muscle contractile measurements (Supplemental data). The EDL muscle was completely removed from the animal and the proximal and distal tendons of the muscle were tied with suture. The muscle was immersed in a bath containing Krebs' mammalian Ringer solution with 0.25 mM tubocurarine chloride. The solution was maintained at 25° C. and bubbled with 95% $O_2$ and 5% $CO_2$. The distal tendon was attached to a servomotor (model 305B, Aurora Scientific, Aurora, ON). The proximal tendon was attached to a force transducer (model BG-50, Kulite Semiconductor Products, Leonia, NJ). The muscle was stimulated by square-wave pulses delivered by two platinum electrodes connected to a high-power biphasic current stimulator (model 701B, Aurora Scientific, Aurora, ON). The voltage of pulses was increased, and optimal muscle length ($L_o$) was subsequently adjusted to produce maximum twitch force. Muscles were held at $L_o$ and stimulus frequency was increased until the Po was achieved. The $sP_o$ was determined by dividing $P_o$ by the cross-sectional area (CSA). The $L_f$-to-$L_o$ ratios of 0.44 for EDL muscles was used to calculate $L_f$. The physiological CSA of muscles was determined by dividing the mass of the muscle by the product of $L_f$ and 1.06 g/cm$^3$, the density of mammalian skeletal muscle.

Statistical analysis. All data are expressed as mean±SEM. Statistical analyses were performed using the GraphPad Prizm software package. Statistical tests used for each experiment, and accompanying N's, are indicated in the Figure Legends.

MYOT knockdown improved histopathology and muscle weight in 3-month (3-mo) old TgT57I mice TgT57I mice recapitulate the progressive MYOT protein aggregation defects that characterize LGMD1A. In 3 mo-old TgT57I mice, aggregates are associated with additional generalized muscle pathology, including deficits in myofiber size and gastrocnemius muscle weight, as well as slight but significant increase in myofibers with centrally located nuclei, which is a histological indicator that muscles underwent degeneration and were subsequently repaired. Importantly, these phenotypes are useful outcome measures for RNAi therapy. We therefore examined the effects of miMYOT-mediated MYOT gene silencing on aggregate formation, myofiber diameter, muscle weight, and central nuclei defects associated with LGMD1A in young adult TgT57I mice.

Aggregate accumulation was examined by staining AAV6.miMYOT—and AAV6.control-treated TgT57I gastrocnemius muscle cryosections with MYOT immunoreactive antibodies, trichrome, and hematoxylin and cosin (H&E) (FIGS. 4A and B). Microscopic image analysis showed that MYOT knockdown significantly reduced the abundance of protein aggregates by 69% in 3-mo old TgT57I gastrocnemius muscles (FIGS. 4B and C).

Next, the impact of MYOT inhibition on cross-sectional myofiber size was determined using H&E stained muscle cryosections. Myofibers from AAV.control-treated TgT57I muscles were significantly smaller (49.9 μm average diameter; p<0.05) than those from either wild-type group (57.0 μm and 57.7 μm in wild-type mice receiving miMYOT or miGFP, respectively; FIG. 4D). In contrast, MYOT knockdown by our therapeutic AAV6.miMYOT vectors improved average myofiber diameter in TgT57I mice by 4.9 μm (a 9.8% improvement), to levels not significantly different than wild-type (54.8 μm in AAV6.miMYOT-treated TgT57I mice; FIG. 4D). This improvement in myofiber size defects evident at the cellular level translated to whole muscle as well. Indeed, weights of AAV6.miMYOT-treated TgT57I gastrocnemius muscles were not significantly different than those measured in wild-type treated controls, while TgT571 muscles that received control AAV6.miGFP vector weighed an average of 15.9 mg less (11% decrease) than their wild-type counterparts (p<0.001; FIG. 4E). Finally, comparing the AAV6.miMYOT—and AAV6.miGFP-treated TgT57I animals, that MYOT knockdown improved 3-mo TgT57I gastrocnemius muscle weight by an average of 9.5 mg, representing a significant 7.1% improvement (p<0.001).

As a final measure of the effects of MYOT knockdown on LGMD1A-associated histopathology in 3-mo old TgT57I mice, the percentage of myofibers containing centrally-located nuclei was quantified. Typically ~98-99% of myonuclei in uninjured wild-type muscles are localized to the cell periphery. Consistent with this, gastrocnemius muscles from our AAV6.miMYOT—and AAV6.miGFP-treated wild-type animals showed 1.1% and 1.9% central nuclei, respectively. In contrast, 7.7% of 3-mo TgT571 myofibers from control AAV6.miGFP-treated gastrocnemius muscles contained central nuclei. This value is consistent with mild degeneration and regeneration in dystrophic animals. Importantly, MYOT knockdown by AAV6.miMYOT reduced the percentage of myofibers with central nuclei to 3.6% in TgT571 mice, representing a significant 2.1-fold decrease (p<0.001; FIG. 4F).

MYOT knockdown also improves histopathology, muscle weight, and specific force in 9-mo old TgT57I mice Gastrocnemius is among the most severely involved muscles in TgT571 mice and LGMD1A patients. Considering this, prospective LGMD1A-targeted therapies should ideally treat gastrocnemius muscle weakness related to mutant MYOT accumulation. Although 3-mo old TgT57I muscles display LGMD1A-associated changes in histology and weight, our pilot studies showed that significant muscle weakness did not manifest until later in adulthood (9 months of age; data not shown). Therefore, a second cohort of animals were treated with with AAV6.miMYOT.1321 or control AAV6.miLacZ vectors for 9 months, with the goal of correcting whole muscle functional deficits in aged TgT57I gastrocnemius muscles.

Before measuring specific force, MYOT suppression by AAV6.miMYOT (79% mRNA; 63% protein; FIG. 1c) was confirmed to be still benefitting TgT57I animals at 9-months of age, using the outcome measures established in our younger, 3-mo cohort. AAV6.miMYOT-treated TgT57I animals showed significant correction by all measures, compared to AAV6.miLacZ control-treated counterparts. Specifically, in 9-mo old AAV6.miMYOT-treated TgT57I animals, aggregates were reduced by 52% (p<0.01); myofibers were 9.1 μm (20%) larger (54 μm average versus 44.9 μm average in AAV6.miLacZ-treated TgT57I; p<0); gastrocnemius muscles weighed 12% more (116 mg average versus 101 mg average in AAV6.miLacZ-treated TgT57I; p>0.002); and central nuclei were reduced 1.5-fold (10.6% in AAV6.miMYOT-treated versus 15.5% in AAV6.miLacZ-treated TgT57I; p<0.04). The improvements afforded by AAV6.miMYOT were partial, as TgT57I animals treated with this therapeutic vector were still significantly different from wild-type groups using all outcome measures at 9-mos (FIG. 5).

Importantly, MYOT knockdown by AAV6.miMYOT caused significant functional improvement in Tg57I gastrocnemius muscles, as determined by whole muscle physiology tests. Specifically, MYOT knockdown improved absolute and specific force in 9-mo TgT57I gastrocnemius muscles by 38% and 25%, respectively (FIG. 5). As with the other outcome measures described above, this represented a partial functional recovery, as both groups of TgT57I animals were significantly different from their wild-type treated counterparts (FIG. 6).

Example 7

Dose Escalation and Self-Complementary AAV (scAAV) Vectors

The U6.miMYOT. 1321 construct was inserted in a scAAV-6 vector [McCarty et al., Gene Therapy, 8 (16): 1248-1254 (2001)]. The U6.mi1321 sequence was PCR amplified from the original single-stranded AAV backbone using PCR primers designed with SpeI sites to each end. This U6.miMYOT.1321 sequence flanked by SpeI sites was then ligated into the scAAV-6 backbone at the SpeI site.

An IM dose escalation ($3 \times 10^9$, $3 \times 10^{10}$, $1 \times 10^{11}$, $1 \times 10^{12}$ DRP) of scAAV.miMYOT.1321 was then performed in wild-type mouse muscle to define a preliminary toxic threshold. Animals receiving doses less than $1 \times 10^{12}$ (that is, $1 \times 10^{11}$, $3 \times 10^{10}$, $3 \times 10^9$) showed no to very little evidence of inflammatory response or overt muscle damage, indicating that doses below $1 \times 10^{12}$ are safe using this delivery route.

Next, $1 \times 10^{11}$ DRP of ss and scAAV.miMYOT were administered to contralateral legs of adult T57I mice, and MYOT protein expression was compared by Western blot 4 weeks later. Adult mice were injected into the left TA muscle with $1 \times 10^{11}$ DRP of single-stranded or self-comp AAV6.miMYOT. The contralateral leg functioned as an uninjected control. Identical doses of scAAV.miMYOT vectors doubled MYOT silencing compared to ssAAV vectors, supporting that dose escalation can safely increase knockdown and may subsequently improve correction in T57I mice.

Example 8

Recombinant AAV Encoding miRNAs with Base Pair Mismatches.

Three miMYOT miRNAs were made that are predicted to have fewer binding sites on transcripts in both the mouse and human genome, compared to the miMYOT-1321 sequence. Each miRNA includes a single base pair mismatch as shown in the right hand side of FIG. 7 by a yellow line between the mismatched nucleotides.

```
miMYOT-1043
                                     (SEQ ID NO: 11286)
CTCGAGTGAGCGATGCCAGAGAACATGTCGATTGCCGTAAAGCCACAGAT

GGGTAATCGACATGTTCTCTGGCACCGCCTACTAGA miMYOT-1044
                                     (SEQ ID NO: 11287)
CTCGAGTGAGCGCGCCAGAGAACATGTCGATTGACCGTAAAGCCACAGAT

GGGTTAATCGACATGTTCTCTGGCACGCCTACTAGA miMYOT-1634
                                     (SEQ ID NO: 11288)
CTCGAGTGAGCGCAGCAGTTACGGGTTCGACTAACTGTAAAGCCACAGAT

GGGTTGGTCGAACCCGTAACTGCTTCGCCTACTAGA
```

The miRNAs were generated by PCR by the methods similar to those described in Example 1. The PCR primers used had the following sequences.

```
Primer 904 (miMYOT-1043-Forward)
                                     (SEQ ID NO: 11289)
AAAACTCGAGTGAGCGATGCCAGAGAACATGTCGATTGCCGTAAAGCCAC

AGATGGG

Primer 905 (miMYOT-1044-Reverse)
                                     (SEQ ID NO: 11290)
AAAAACTAGTAGGCGGTGCCAGAGAACATGTCGATTACCCATCTGTGGCT

TTACGG

Primer 906 (miMYOT-1044-Forward)
                                     (SEQ ID NO: 11291)
AAAACTCGAGTGAGCGCGCCAGAGAACATGTCGATTGACCGTAAAGCCAC

AGATGGG

Primer 907 (miMYOT-1044-Reverse)
                                     (SEQ ID NO: 11292)
AAAAACTAGTAGGCGTGCCAGAGAACATGTCGATTAACCCATCTGTGGCT

TTACGG

Primer 902 (miMYOT-1634-Forward)
                                     (SEQ ID NO: 11293)
AAAACTCGAGTGAGCGCAGCAGTTACGGGTTCGACTAACTGTAAAGCCAC

AGATGGG

Primer 903 (miMYOT-1634-Reverse)
                                     (SEQ ID NO: 11294)
AAAAACTAGTAGGCGAAGCAGTTACGGGTTCGACCAACCCATCTGTGGCT

TTACAG
``` scAAV encoding the miRNAs were then made. The scAAV.miMYOT.1321 vector described in Example 7 was digested with SpeI and NotI to remove the U6.miMYOT.1321 sequence. SpeI and NotI restriction sites were added to the tMCK promoter by PCR with primers containing the sites. The tMCK promoter PCR product was ligated then ligated into the same sites in the digested U6.miMYOT.1321 vector, resulting in a scAAV vector containing the tMCK promoter but with no miRNA sequences (scAAV.tMCK). To add miRNAs, double-stranded DNA oligonucleotides containing miRNA sequences were designed with XhoI and EcoRI sites, and subcloned into the XhoI and EcoRI sites of the pSM2/CMV vector (www.addgene.org/17389/). This subcloning step added pri-mir-30 flanking sequences to the respective miRNAs. The miRNAs in pSM2/CMV were then PCR amplified using primers containing NotI and SacII sites, and subcloned into the same sites located after the tMCK promoter in the scAAV.tMCK vector. The scAAV including a genome encoding the MYOT miRNA set out in SEQ ID NO: 11286 was named "scAAV-tMCK-miMyoT-1043", the rAAV including a genome encoding the MYOT miRNA set out in SEQ ID NO: 11287 was named "scAAV-tMCK-iMyoT-1044") and the rAAV including a genome encoding the MYOT miRNA set out in SEQ ID NO: 11288 was named "AAV-tMCK-miMyoT-1634."

The effect of the three miRNAs on MyoT expression in cells was examined. HEK293 cells were co-transfected with plasmids expressing human myotilin and the U6.miMYOT sequences using Lipofectamine-2000. Protein was harvested from cells the next day using M-PER buffer, quantified by Lowry assay, and then resolved with SDS-PAGE electrophoresis. Protein was transferred to PVDF membrane and blots were incubated with anti-MYOT and anti-GAPDH (loading control) antibodies, followed by HRP-coupled secondary antibodies and development on film using chemiluminescence. FIG. 7 includes a Western blot showing each miRNA reduces MyoT protein to levels similar to the miMYOT-1321 miRNA.

While the present invention has been described in terms of specific embodiments, it is understood that variations and modifications will occur to those skilled in the art. Accordingly, only such limitations as appear in the claims should be placed on the invention.

All documents referred to in this application are hereby incorporated by reference in their entirety.

SEQUENCE LISTING

The patent contains a lengthy sequence listing. A copy of the sequence listing is available in electronic form from the USPTO web site (https://seqdata.uspto.gov/?pageRequest=docDetail&DocID=US12325856B2). An electronic copy of the sequence listing will also be available from the USPTO upon request and payment of the fee set forth in 37 CFR 1.19(b)(3).

We claim:

1. A recombinant adeno-associated virus encoding a myotilin (MYOT) microRNA (miRNA) comprising an antisense guide strand as set out in any one of SEQ ID NOs: 7701, 7798, 7945, 7967, 7990, 8057, 8078, and 8148, wherein the recombinant adeno-associated virus lacks rep and cap genes.

2. A composition comprising the recombinant adeno-associated virus of claim 1 and a carrier, diluent, and/or adjuvant.

3. The recombinant adeno-associated virus of claim 1, wherein the recombinant adeno-associated virus (rAAV) is rAAV-6.

4. The recombinant adeno-associated virus of claim 3, wherein the rAAV-6 is self-complementary rAAV-6.

5. A method of inhibiting expression of the myotilin (MYOT) gene in a cell comprising contacting the cell with an effective amount of the recombinant adeno-associated virus of claim 1.

6. A method of delivering a myotilin (MYOT) miRNA-encoding DNA to an animal in need thereof, comprising administering to the animal an effective amount of the recombinant adeno-associated virus of claim 1.

7. A method of treating limb girdle muscular dystrophy type 1A in a subject comprising administering to the subject an effective amount of the recombinant adeno-associated virus of claim 1.

8. The method of claim 5, wherein the recombinant adeno-associated virus is a self-complementary rAAV-6.

9. The method of claim 6, wherein the recombinant adeno-associated virus is a self-complementary rAAV-6.

10. The method of claim 7, wherein the recombinant adeno-associated virus is a self-complementary rAAV-6.

* * * * *